United States Patent [19]

Bertolucci

[11] Patent Number: 4,981,146

[45] Date of Patent: Jan. 1, 1991

[54] NAUSEA CONTROL DEVICE

[75] Inventor: Lawrence E. Bertolucci, Citrus Heights, Calif.

[73] Assignee: Maven Labs, Inc., Sacramento, Calif.

[21] Appl. No.: 475,985

[22] Filed: Feb. 6, 1990

Related U.S. Application Data

[63] Continuation of Ser. No. 323,219, Mar. 10, 1989, which is a continuation-in-part of Ser. No. 184,193, Apr. 21, 1988, abandoned.

[51] Int. Cl.$^5$ .................................................. A61N 1/32
[52] U.S. Cl. ...................................... 128/802; 128/907; 128/421
[58] Field of Search ............... 128/783, 796, 802, 419 S, 128/421, 387, 907, 82.1, 791, 794, 795, 419 C; 600/26; 604/20

[56] References Cited

U.S. PATENT DOCUMENTS

| 3,289,671 | 12/1966 | Troutman et al. | 604/20 |
|---|---|---|---|
| 3,412,731 | 11/1968 | Reynolds | 604/20 |
| 3,480,010 | 11/1969 | Crossley | 128/802 |
| 3,565,080 | 2/1971 | Ide | 128/783 |
| 3,857,397 | 12/1974 | Brosseau | 128/384 |
| 3,885,576 | 5/1975 | Symmes | 128/802 |
| 4,147,171 | 4/1979 | Green et al. | 128/421 |
| 4,210,150 | 7/1980 | James | 128/421 |
| 4,398,545 | 8/1983 | Wilson | 128/421 |
| 4,509,531 | 4/1985 | Ward | 128/738 |
| 4,561,851 | 12/1985 | Ferreira et al. | 128/421 |
| 4,664,118 | 5/1987 | Batters | 128/802 |
| 4,715,367 | 12/1987 | Crossley | 128/419 R |
| 4,722,343 | 2/1988 | Lombardi | 128/421 |

FOREIGN PATENT DOCUMENTS

| 0257989 | 3/1988 | European Pat. Off. | 128/907 |
|---|---|---|---|
| 2721395 | 11/1978 | Fed. Rep. of Germany | 128/802 |
| 3618933 | 12/1986 | Fed. Rep. of Germany | 128/791 |
| 3609536 | 3/1987 | Fed. Rep. of Germany | 128/802 |
| 3634097 | 4/1988 | Fed. Rep. of Germany | 128/802 |
| 8607269 | 12/1986 | PCT Int'l Appl. | 604/20 |
| 0725671 | 4/1980 | U.S.S.R. | 128/421 |
| 0997670 | 7/1965 | United Kingdom | 128/907 |

Primary Examiner—Max Hindenburg
Assistant Examiner—Kennedy J. Schaetzle
Attorney, Agent, or Firm—Kelly Bauersfeld & Lowry

[57] ABSTRACT

A nausea control device is provided in the form of a watch-like housing and related attachment band for mounting onto the human wrist, wherein the device includes electronic circuitry for imparting electrical impulses via positive and negative electrodes to the percardium six (P6) acupuncture point for alleviating nausea. Batteries within the housing power the electric circuitry, and a manually operable switch on the housing controls on/off and pulse amplitude.

16 Claims, 4 Drawing Sheets

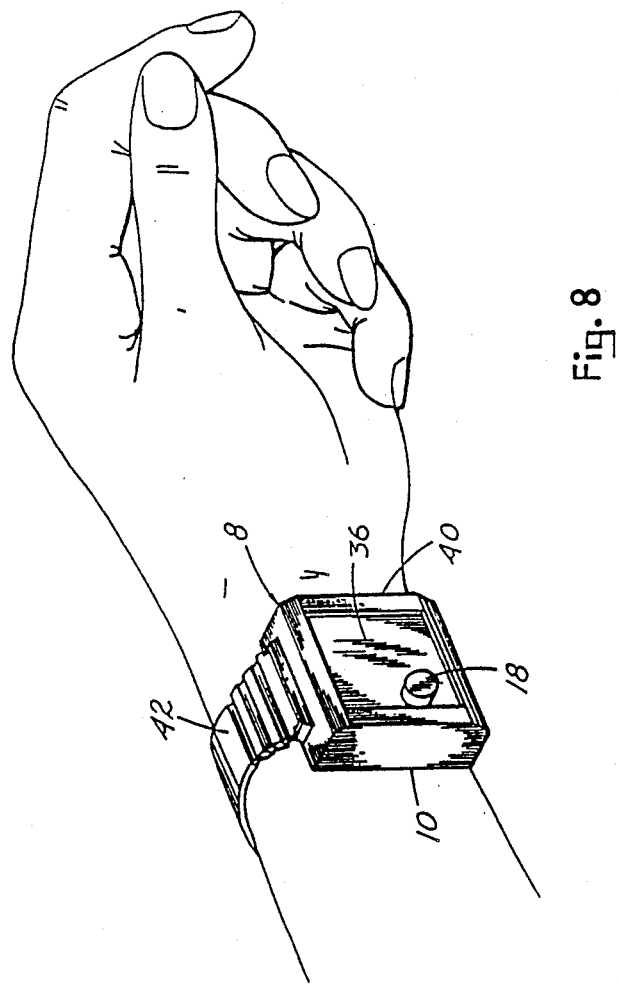

NAUSEA CONTROL DEVICE

This application is a continuation of copending Ser. No. 323,219 filed Mar. 10, 1989, which in turn is a continuation-in-part of application Ser. No. 184,193, filed Apr. 21, 1988, and now abandoned.

BACKGROUND OF THE INVENTION

1. Field of the Invention

This invention relates to non-chemical means for reducing and alleviating nausea. The invention utilizes electrical current passed through an acupuncture site on the human body for the control of nausea.

2. Description of the Prior Art

Although there are many effective anti-nausea medications available today, there are also drawbacks associated with the use of chemical compositions. Many people are allergic to some chemical medications and therefore cannot use this form of treatment to alleviate nausea. Consequently, the need to relieve nausea by means other than chemical medications has developed. The use of acupuncture and acupressure has effectively been in use for many centuries in other countries for this and other medical purposes. Acupuncture and acupressure are traditional Chinese therapeutic techniques involving the stimulation of certain nerves and nerve junctions by puncturing the skin with fine needles or manual massage and pressure of those same nerve junctions to produce a certain physiological effect. The exact means by which this is accomplished is unclear, but the results are conclusive.

A patent search was conducted to examine non-chemical means for reducing and alleviating nausea. The search was focused on the following U.S. classes and subclasses: 128/72, 381, 769, 800, 798, 802, 419R, and 419S.

The following prior art patents were located in the course of the patent search, and are considered to be the references most pertinent to my invention The Wilson U.S. Pat. No. 4,398,545, issued on Aug. 16, 1983, illustrates a device designed to block pain impulses originating from an injury;

The Hoffmann U.S. Pat. No. 3,107,672, and the Moss U.S. Pat. No. 3,424,165, are directed toward stimulating and firming the muscles for cosmetic purposes;

Oseau U.S. Pat. No. 3,911,910, issued on Oct. 14, 1975, teaches a device designed to relieve involuntary muscle spasticity;

The Symmes U.S. Pat. No. 3,889,163, the Fischell U.S. Pat. No. 4,440,160, and the Crossley U.S. Pat. No. 4,715,367, teach devices which assist in refraining from undesirable habits. These devices utilize painful or alarming electrical stimulation.

Hathaway U.S. Pat. No. 2,223,447 illustrates a non-portable radiotherapy system designed for treatment of certain diseases.

None of the prior art patents examined are specifically structured as fully self-contained and portable wearable devices for reducing or eliminating nausea. Some of the prior art devices are directed toward stimulating a general area of the body or a muscle or muscle group and are not designed to stimulate specific nerves to alleviate nausea. Other devices examined are designed to produce an irritating or even painful electric impulse to produce a certain desired response in the person wearing the device. Pain used for behavior modification is not the object of my invention. Several of the prior art devices require administration by one experienced and skilled with the equipment, whereas my device is simple and easy to use, requiring no special training or experience.

My device is primarily directed towards stimulating the pericardium six acupuncture point (known as "P6") or the master point of the vascular meridian located in the human wrist for the purpose of alleviating nausea. The invention is completely portable and fully self-contained. It can also be safely and painlessly self-administered.

SUMMARY OF THE INVENTION

In practicing my invention, I have developed a fully self-contained electric nerve stimulator with electronic means contained within a watch-like housing attachable to the human wrist by an adjustable attachment band. The device is designed primarily for stimulating the master point of the vascular meridian located in the human wrist to effectively control nausea. Acupuncture or acupressure stimulation of this acupuncture point has been shown to relieve migraines, visceral organ pain, and nausea. My device utilizes electricity passed through two electrodes to stimulate the P6 or master point of the wrist. An electrical repetition rate of approximately 70 pulses per second and a pulse width of 80 microseconds has been found to provide effective relief of nausea in a human subject.

In a first embodiment of the invention, a first electrode is affixed to the attachment band and a second electrode is attached to the bottom of the housing which contains operational electronics. In a second embodiment of the invention both electrodes are attached to the bottom of the housing in spaced relation to each other. Both electrodes could be attached to he band and would function equally well. In any fixed arrangement of the electrodes of the invention, the current flow can only provide stimulation to a point between the two electrodes.

The invention is physically small and powered by batteries allowing it to be completely self-contained and portable. In this regard, the two electrodes can only provide stimulation to a point between them, such that indiscriminant use of the device is avoided on other areas of the body whereat such treatment may be undesired, for example, over the abdominal area of a pregnant women. An optional stretchable water repellant cover is available for use in wet weather for greater protection of the electronics of the device.

Therefore, a primary object of my invention is to provide a non-chemical, non-invasive, painless and inexpensive method of alleviating nausea.

Another object of my invention is to provide a nausea control device which is safe and easy to use, and which can be safely self-administered without lengthy instruction, with little or no risk of misuse.

A further object of my invention is to provide a nausea control device which is portable, self-contained, and non-cumbersome to the human subject.

A still further object of my invention is to provide a nausea control device which alleviates nausea symptoms associated with a variety of conditions such as morning sickness generated by pregnancy, motion sickness, and nausea resulting from various cancer treatments.

Other objects and advantages of my invention will prove evident from a reading of the specification and comparison of the drawings with the drawing reference numbers.

BRIEF DESCRIPTION OF THE DRAWINGS

In the drawings:

FIG. 8 is a perspective illustration of the embodiment of FIG. 6 as worn on the wrist of a person using the device to suppress nausea.

DESCRIPTION OF THE PREFERRED EMBODIMENT

Figure 6:
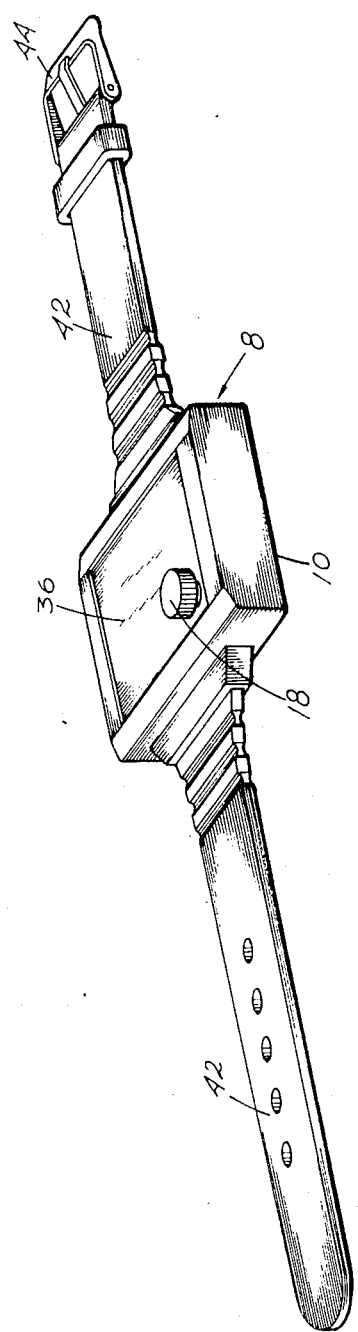
FIG. 6 is a perspective view showing an alternative preferred embodiment of the invention.
Figure 7:
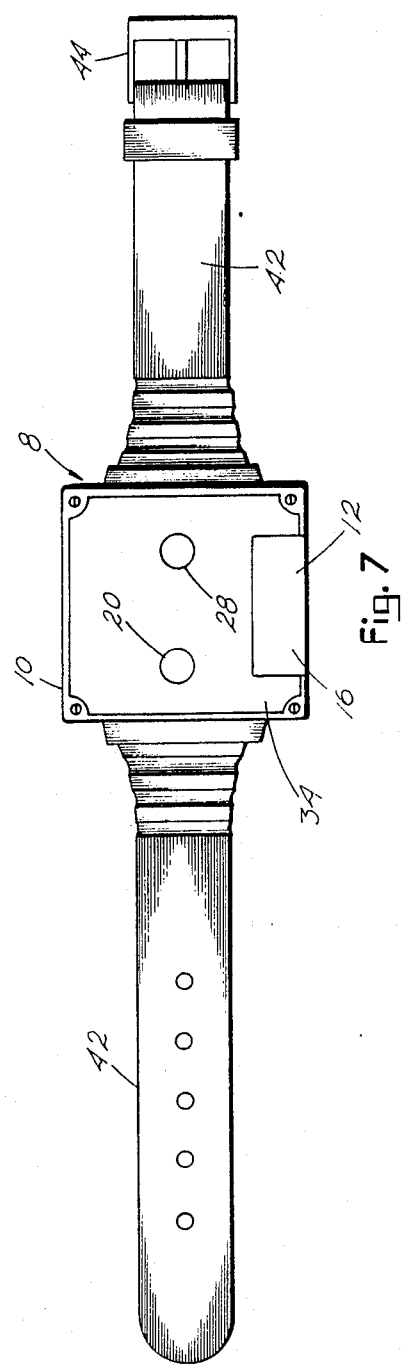
FIG. 7 is a bottom plan view of the embodiment of FIG. 6.

Referring now to the drawings in general where two examples of the invention are shown with one example designated first embodiment 6 (FIGS. 1 and 2) and the other example designated second embodiment 8 (FIGS. 6-8). Common reference numerals will be utilized throughout these descriptions and the accompanying drawings to identify functionally common components of both embodiments 6 and 8.

The main power directing and operational electronics for the invention are located within a watch-like housing 10. Housing 10 is preferably structured of rigid electrically non-conductive plastic in order to electrically insulate attached electrodes from the surrounding structures and each other, as will be explained in more detail. Housing 10 may be manufactured in a multitude of shapes, but should be sized similar to that of a wristwatch housing to allow placement against a human wrist. In the drawings, housing 10 is shown as a rectangular structure having four short vertical sidewalls attached between a housing bottom surface 34 and a housing top surface 36.

Figure 1:
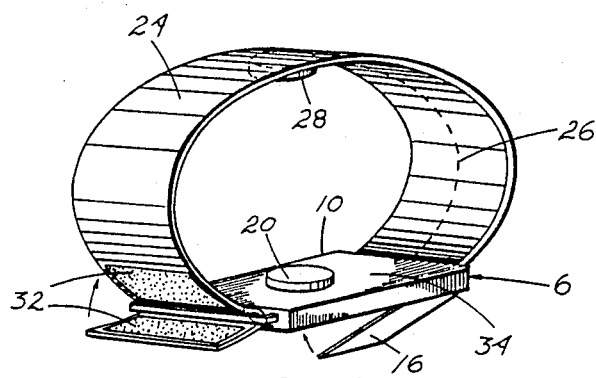
FIG. 1 is a perspective view of one preferred embodiment shown in an inverted position.
Figure 2:
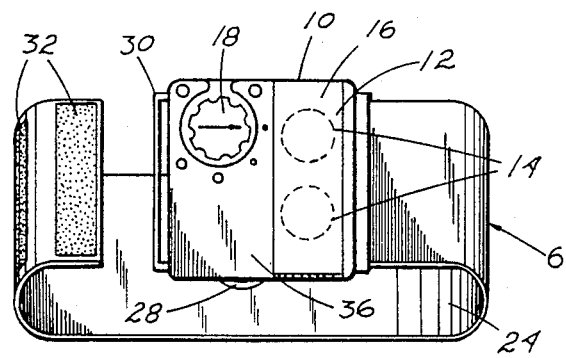
FIG. 2 is a top plan view of the embodiment depicted in FIG. 1.

A battery compartment 12 is formed within housing 10 and is accessible through an openable battery compartment cover 16 located in the housing top surface 36 as shown in FIGS. 1 and 2, or in the housing bottom surface 34 as shown in FIG. 7. Future structuring of the invention will most likely utilize permanent rechargeable batteries circuited to an electrical jack on housing 10 for receiving low voltage current from an electrical plug wired to an external transformer (not shown). In any event, the batteries 14 currently used in the invention are removably housed within battery compartment 12 and provide the operational power for the invention.

Figure 3:
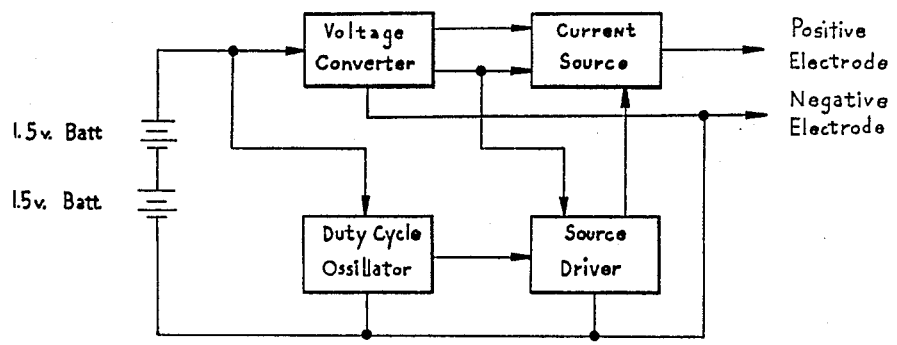
FIG. 3 is a block diagram of the electrical circuitry commonly used in the invention.

The pair of batteries 14 depicted in FIG. 3 are connected in series to provide an initial operating voltage source of 3 volts. The power from batteries 14 is circuited to drive a high voltage converter and a duty cycle oscillator, shown in FIG. 3 where the major power directing and operational electronics for the invention are shown in a block diagram. The high voltage converter consists of a high frequency oscillator of approximately 100 kilohertz and is used to drive a step-up voltage transformer. The step-up transformer provides a 40 volt pulsed voltage source which is rectified and filtered to provide a 40 volt DC supply. The duty cycle oscillator is an astable oscillator having preset programming to render an off-time of about 14.3 milliseconds and an on-time of 80 microseconds. The duty cycle oscillator drives a current source driver that converts a low voltage output signal of the duty cycle oscillator into a high voltage signal needed to drive a high voltage current source. The current source is configured to provide a variable amplitude current pulse into a 500 ohm AAMI or resistive load. The substantial part of the discharge life of batteries 14 occurs at 2.4 volts giving a maximum current pulse amplitude of about 50 milliamperes. Shown in the block diagram in FIG. 3 is a normally open output circuit being opened between a positive electrode and a negative electrode. The normally opened output circuit receives the high voltage output of the operational electronics held in housing 10. The variable current pulse amplitude control is provided by a variable resistor in the current flow through the normally open output circuit when closed. Located on housing top surface 36 is an accessible rotary control knob 18 allowing manual setting of the current pulse amplitude. Though the circuitry is capable of providing 0-70 milliamperes at full battery charge, current limiting is provided to keep the maximum current pulse amplitude at the 50 milliampere level consistent with the normal battery operating conditions. Control knob 18 also serves as an on/off switch to control current flow between batteries 14 and the operational electronics held in housing 10.

Referring now more specifically to first embodiment 6 where negative electrode 20 is electrically connected to a first side of the normally open output circuit of the operational electronics shown in FIG. 3 for negative charging. Negative electrode 20 is affixed centrally on housing bottom surface 34 adapted to contact with exterior surface 22 of the wrist (FIG. 4) of a human subject when in use. Extending outward from one sidewall of housing 10 and permanently attached thereto is attachment band 24. Attachment band 24 is comprised of two elongated permanently laminated equally sized substantially rectangular straps. The rectangular straps are manufactured of a flexible, water resistant plastic material having electrical insulating properties. Encased between the two laminated straps of attachment band 24 is insulated flexible conductor 26 (FIG. 1). Attachment band 24 containing conductor 26 may be manufactured using a variety of other known methods such as thermoplastic injection of the plastic of band 24 around conductor 26. Flexible conductor 26 is electrically connected to positive electrode 28, which comprises a second electrode affixed approximately three inches from housing 10 on the interior surface of attachment band 24. Positive electrode 28 is affixed to attachment band 24 positioned to contact the interior surface 40 of the wrist when in use. Flexible conductor 26 extends from where it attaches to positive electrode 28, lengthwise toward the housing and enters the housing 10 and attaches to a second side of the normally open output circuit of the electronics within housing 10 for positive charging of electrode 28. The normally open output circuit is maintained open by spacing and the dielectric material between electrodes 20 and 28 in the circuit.

Partial adjustability of attachment band 24 is accomplished by leaving one end free for removable and adjustable attachment to band retaining slot 30 (FIG. 2).

Band retaining slot 30 is structured of an elongated bar permanently attached to the outward edges of one side of housing 10 by short braces. Band retaining slot 30 is positioned oppositely across housing 10 from the permanent attach location of attachment band 24, and is a cooperatively sized fixture to accommodate the insertion of the free end of attachment band 24. The attachment system on the free end of band 24 uses a standard hook and loop fastener 32 or other suitable means to provide for limited circumferential adjustability around a human wrist. When the free end of attachment band 24 is inserted through band retaining slot 30, a loop is formed around the subject's wrist with positive electrode 28 positioned generally oppositely the negative electrode 20.

In use, first embodiment 6 is applied over the wrist with housing 10 positioned over either the exterior or interior surface of the wrist. The free end of attachment band 24 is brought under the wrist and looped through band retaining slot 30. Adjustment is made to attachment band 24 by hook and loop attachments 32 to somewhat center positive electrode 28 beneath negative electrode 20. Both electrodes are substantially centered over the P6 master acupuncture point. The attachment of the invention to the wrist causes electrodes 20 and 28 to contact the wrist simultaneously, completing the normally open output circuit.

The device is then switched on by rotating manually operable control knob 18. The high voltage applied to the now closed normally open output circuit is sufficient to cause current flow between electrodes 20 and 28 by way of flowing through the wrist. The operational electronics will continually automatically pulse a constant level of current through the output circuit. Due to the insulated mountings and the insulated circuit conductors attached to electrodes 20 and 28, the only flow path for the current flow in the now closed normally open output circuit is through the flesh of the wrist. The current flowing through the wrist flows through or adjacent the P6 master acupuncture point with the current flowing from negative electrode 20 through the wrist to positive electrode 28. The current flow stimulates the area of the wrist containing the P6 master acupuncture point and is quite effective in reducing nausea. Increasing the current pulse amplitude increases the anti-nausea effect of the invention. Desired variations of the current pulse amplitude may be controlled by the subject by rotating control knob 18. Through controlling the current pulse amplitude by way of control knob 18, the subject can reduce the current flow from a very low level which is hardly detectable, to a much higher level. Excessively high levels of current flow may cause slight discomfort to some patients.

Although electrode 20 has been described as the negative electrode, and electrode 28 as the positive electrode, during operation the polarity of either of the two electrodes is non-critical as long as one is charged negatively and the other positively by the operational electronics in housing 10.

Second embodiment 8 of my invention is shown in FIGS. 6 and 8 in the drawings. Although identical in function and basic circuitry to that of embodiment 6, embodiment 8 differs slightly in electrode placement. Second embodiment 8 is structured with substantially the same housing 10. Housing top surface 36 of second embodiment 8 also has control knob 18 serving as an on/off switch and means for controlling the current pulse amplitude. The housing 10 also contains batteries 14 which are replaceable by way of openable battery compartment cover 16.

The major difference between embodiments 6 and 8 is that embodiment 8 has both negative electrode 20 and positive electrode 28 attached in spaced relation to each other at the bottom surface 34 of housing 10, a structure which is slightly more cost effective to manufacture than embodiment 6. Embodiment 8 is primarily designed to be worn with the electrodes 20 and 28 disposed at the interior surface 40 of the wrist where best results may be obtained for nausea control. However, limited results may also be obtained by contacting the two electrodes against the exterior 22 of the wrist. The two electrodes are spaced apart about 1" and are electrically insulated from each other by the dielectric material of housing bottom surface 34 or by using other suitable insulating means. Housing 10 is connected to the wrist by flexible attachment straps 42. Attachment straps 42 are similar in structure and function to a conventional wristwatch bands and may be manufactured in a wide variety of known styles and materials. The materials used to manufacture straps 42 need not necessarily be dielectric in this embodiment. Attachment straps 42 of second embodiment 8 are illustrated in the drawings using a common buckle type fastener 44.

In use, second embodiment 8 is affixed to the wrist by attachment straps 42 with housing 10 positioned adjacent interior surface 40 of the wrist. The electrical current is passed from one electrode to the other by passing directly across and through the flesh of the wrist. The flow of current stimulates the area of the wrist containing the P6 master acupuncture point and is quite effective in controlling nausea.

The direct current pulsed through electrodes 20 and 28 of the output circuit of which the wrist is a necessary electrical link has been found to reduce nausea more effectively than non-pulsing current. However, non-pulsing current has also been shown to be somewhat effective in reducing nausea when used in the invention.

Figure 4:
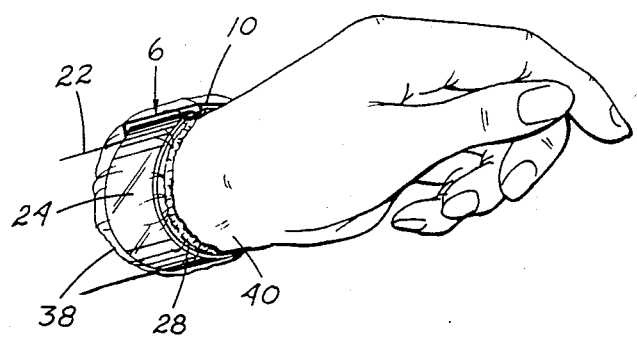
FIG. 4 illustrates the embodiment of FIG. 1 in use with an optional water repellant stretchable cover.
Figure 5:
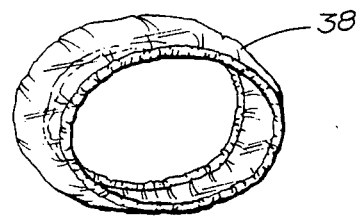
FIG. 5 is a perspective illustration of the water repellant stretchable cover.

Although both electrical nerve stimulation embodiments shown are manufactured using water tight methods and materials to prevent the entrance of liquids, an optional water repellant stretchable cover 38 shown in FIGS. 4 and 5 may be used. Cover 38 is designed to be used in wet or rainy locations for added protection of the electronics of the device.

Some anticipated modifications which could be made to the invention are various positioning of the electrodes on the attachment band and housing; separate control knobs for power on/off and current pulse amplitude control; various operating voltages and frequencies of the electronics; and various attachment band arrangements.

I have described my invention in considerable detail in the specification and consequently modifications in the structure will be obvious to those skilled in the art after reading this disclosure. Therefore, when those modifications fall within the intended scope of the appended claims I will consider that modified structure to be my invention.

What is claimed is:

1. A nausea control device for suppressing nausea by electrical stimulation of the pericardium six (P6) acupuncture point at a human wrist, said device comprising:

a wristwatch-like housing having a size and shape adapted to be worn on the human wrist;

a pair of electrodes carried by said housing in spaced relation to each other;

circuit means mounted within said housing and electrically coupled to said electrodes, said circuit means having means for delivering a pulsed electrical stimulation signal of selected amplitude and cycle rate to said electrodes; and wristband means connected to said housing and adapted to be fastened about the human wrist to orient said housing and said electrodes in a position generally closely overlying the P6 acupuncture point, such that said stimulation signal delivered to said electrodes stimulates the wrist generally at the P6 acupuncture point to suppress nausea.

2. The nausea control device of claim 1 wherein said electrodes are carried by said housing in a spaced side-by-side orientation for contacting a common side of the wrist when the housing is worn on the wrist.

3. The nausea control device of claim 1 wherein said circuit means includes a battery power source.

4. The nausea control device of claim 3 wherein said housing defines an accessible battery compartment, said battery power source being removably received into said compartment.

5. The nausea control device of claim 3 wherein said circuit means further includes an on/off switch.

6. The nausea control device of claim 3 wherein said circuit means includes means for variably adjusting the amplitude of said stimulation signal.

7. The nausea control device of claim 1 wherein said circuit means includes means for delivering said stimulation signal at a cycle rate of about seventy pulses per second.

8. The nausea control device of claim 7 wherein said circuit means includes means for delivering said stimulation signal at a pulse width of about eighty microseconds.

9. The nausea control device of claim 1 wherein said stimulation signal is a pulsed direct current signal.

10. A nausea control device for suppressing nausea by electrical stimulation of the pericardium six (P6) acupuncture point at the human wrist, said device comprising:

a wristwatch-like housing having a battery compartment formed therein;

a pair of electrodes carried by said housing in spaced relation to each other;

wristband means connected to said housing and adapted to be fastened about the human wrist to orient said housing in a position with said electrodes contacting the wrist and generally closely overlying the P6 acupuncture point;

at least one battery removably mounted within said battery compartment; and circuit means within said housing and powered by said at least one battery, said circuit means including means for generating a pulsed direct current stimulation signal at a selected cycle rate, pulse width, and amplitude, said circuit means delivering said stimulation signal to said electrodes to stimulate the wrist generally at the P6 acupuncture point to suppress nausea.

11. The nausea control device of claim 10 wherein said selected cycle rate is about seventy pulses per second, and wherein said pulse width is about eighty microseconds.

12. The nausea control device of claim 11 further including means for adjusting the amplitude of said stimulation signal.

13. A method of controlling nausea, comprising the steps of:

mounting a pair of electrodes onto the human wrist at a position generally closely overlying the pericardium six (P6) acupuncture point;

generating a pulsed stimulation signal of selected amplitude, pulse width and cycle rate; and delivering the stimulation signal to the electrodes to stimulate the wrist generally at the P6 acupuncture point to suppress nausea.

14. The method of claim 13 wherein said mounting step includes mounting a wristwatch-like housing carrying the electrodes onto the wrist with a wristband adapted to be fastened about the wrist, with the housing having circuit means including a portable power supply encased therein for generating the stimulation signal.

15. The method of claim 13 further including the step of adjustably varying the amplitude of the stimulation signal.

16. The method of claim 13 wherein said mounting step includes mounting the electrodes in spaced side-by-side relation onto the wrist.

* * * * *